(12) United States Patent
Kelly et al.

(10) Patent No.: US 6,400,977 B1
(45) Date of Patent: Jun. 4, 2002

(54) UNIVERSAL ELECTROCARDIOGRAM SENSOR POSITIONING DEVICE AND METHOD

(75) Inventors: Robert J. Kelly, Camarillo; William K. Wenger, Laguna Niguel, both of CA (US)

(73) Assignee: Unilead International Inc., Lafayette, CA (US)

( * ) Notice: Subject to any disclaimer, the term of this patent is extended or adjusted under 35 U.S.C. 154(b) by 0 days.

(21) Appl. No.: 09/461,701

(22) Filed: Dec. 14, 1999

Related U.S. Application Data

(63) Continuation of application No. 09/022,730, filed on Feb. 12, 1998, now Pat. No. 6,006,125.

(51) Int. Cl.[7] .............................................. A61B 5/0408
(52) U.S. Cl. ........................ 600/382; 600/391; 600/393
(58) Field of Search ................................ 600/382, 386, 600/388–393

(56) References Cited

U.S. PATENT DOCUMENTS

| | | | | |
|---|---|---|---|---|
| 4,498,480 A | * | 2/1985 | Mortensen | 600/393 |
| 4,538,349 A | * | 9/1985 | Manoli | 600/393 |
| 5,327,888 A | * | 7/1994 | Imran | 600/393 |
| 5,465,727 A | * | 11/1995 | Reinhold, Jr. | 600/390 |
| 5,507,290 A | * | 4/1996 | Kelly et al. | 600/393 |
| 5,678,545 A | * | 10/1997 | Stratbucker | 600/382 |
| 5,782,238 A | * | 7/1998 | Beitler | 600/388 |
| 5,788,238 A | * | 8/1998 | Mahoney | 600/382 |
| 5,868,671 A | * | 2/1999 | Mahoney | 600/382 |

* cited by examiner

*Primary Examiner*—Lee Cohen
(74) *Attorney, Agent, or Firm*—Bruce & McCoy; Ernest H. McCoy

(57) ABSTRACT

A universal disposable ECG sensor positioning device and method for use with electrocardiogram diagnostic equipment in which the mask has nine sensors, six of which can be used at any one time to provide three different sizes to accommodate varying sized human torsos.

6 Claims, 1 Drawing Sheet

UNIVERSAL ELECTROCARDIOGRAM SENSOR POSITIONING DEVICE AND METHOD

This application is a continuation of application Ser. No. 09/022,730 filed on Feb. 12, 1998, now U.S. Pat. No. 6,006,125.

RELATED APPLICATIONS

U.S. patent application Ser. No. 08/508,928, filed Jul. 28, 1995, for a Disposable Electro-Dermal Device, now abandoned.

U.S. patent application Ser. No. 08/783,721, filed Jan. 16, 1997, for an Electrode Equipped Electro-Dermal Device, now U.S. Pat. No. 3,916,159.

U.S. patent application Ser. No. 08/783,912, filed Jan. 16, 1997, for a Disposable Electrodeless Electro-Dermal Device, now U.S. Pat. No. 6,066,093.

U.S. patent application Ser. No. 08/783,904, filed Jan. 16, 1997, for a Disposable Electro-Dermal Device, now U.S. Pat. No. 3,865,741.

BACKGROUND OF THE INVENTION

1. Field of the Invention

The present invention relates to a multiple electrical sensor positioning device. More particularly, it relates to a universal sensor mask and its method of use with diagnostic medical equipment. More particularly still, the present invention relates to a disposable dermal chest mask for assistance in establishing physical attachment of sensors from electrocardiograph machines to a human chest.

2. Description of the Prior Art

Prior art electrodes for contacting a specific area of the human body for use with diagnostic medical equipment are generally a combination of elements. A signal wire from the analytical apparatus is usually attached to a metallic or otherwise conductive body contact electrode which is attached to the patient's skin at the desired point of contact. The wire and electrode combination are generally referred to as a "lead." Electrical current generated by the heart in a person's chest flows to the surface and at the skin produces differences in electrical voltage which can be measured between pairs of electrodes placed at two points on the skin. One of the most common tests performed requiring electrode attachment to a patient's body is an electrocardiogram, sometimes alternatively referred to as an ECG. A twelve-lead electrocardiograph provides the most accurate signals for recognizing ischemic electrocardiographic changes.

To administer a resting twelve-lead ECG, it is necessary to apply ten electrodes to various points on the torso and limbs of a patient to measure and analyze cardiac data. Twelve recordings for the ECG are made from nine active lead positions with the tenth being used as a ground. An electrode portion of a lead may in fact consist of an alternative form of sensor, and the terms "electrode" or "sensor" for purposes of this disclosure are interchangeable. A lead wire connecting a sensor to the diagnostic equipment could possibly in fact consist of a radio or an optical signal. Six of the ten electrodes are applied to the patient's chest over prescribed anatomical landmarks. The remaining four electrodes are applied to each of the patient's limbs. The chest electrodes are known as the precordial leads and the limb electrodes are called limb leads. The precordial leads are designated $V_1$, $V_2$, $V_3$, $V_4$, $V_5$, and $V_6$. The limb leads are designated LA, RA, LL, and RL (ground).

It is generally acknowledged that it is critically important to place the precordial leads with precision in order to obtain accurate and repeatable recordings. However, accurate placement and attachment of a large number of leads can be difficult and time consuming and requires knowledge, skill, and diligence on the part of the person attaching the electrodes or sensors. Mechanical problems in attaching multiple leads to a patient range from tangling of lead wires and excessive time consumed in pairing lead wires with the appropriate electrodes, to difficulty in locating anatomical landmarks on a patient with precision.

Problems occur if the leads are not properly placed and are located higher or lower than optimal. The position of the precordial leads is determined by the anatomical features of the patient's chest and not by the position of the heart itself. Research reported in the electrocardiography literature indicates that precordial leads placed one inch or more from their true anatomical landmarks can result in misinterpretation of the patient's ECG. This may result in or contribute to diagnosis errors, false hospital admissions, sending sick people home, or have other negative impacts on diagnosis or treatment. The placement problem is compounded when serial comparisons are made between two or more ECGs taken over time. For example, if $V_4$ was placed one inch too high for one test and one inch too low for another, the difference of two inches may produce what appears to be a significant difference between the two ECGs when in fact there was no physiological change in the patient's heart condition.

To place the precordial leads accurately requires training in using both visual and palpatory cues to find the anatomical landmarks on each patient. Placement accuracy is also affected by the time and diligence dedicated to placing the precordial electrodes. An experienced and conscientious electrocardiologist may require and devote ten minutes to palpation and ascertaining the exact precordial landmarks. However, in busy clinical environments or emergency situations, medical personnel are often so rushed they may not even palpate the patient. Under those conditions, precordial leads are commonly placed with inadequate palpation and with little attention to a patient's particular anatomy. As a consequence, individual leads are often misplaced by two and as much as three inches from their true anatomical landmarks. In addition, training and maintaining the necessary skill for proper placement of individual leads is time and resource consuming and often not adequate. With six precordial leads, there are six chances to misplace electrodes. Research shows that $V_1$ and $V_2$ electrodes are typically placed high and wide of their targets—the fourth intercostal space on each side of the sternum. Likewise, precordial electrodes $V_4$, $V_5$, and $V_6$ are most often misplaced low and wide. Electrode $V_3$ is most often misplaced too low. The most obvious conclusion to be drawn is that lead placement is often not accurate.

After the individual electrodes are positioned on a patient, it is necessary to attach the ten lead wires. Each lead wire is labeled to correspond to one of the anatomical landmarks, i.e., $V_1$, $V_2$ ... $V_6$ ... RL. Should lead wires be crossed, interpretative ECG monitors can detect and alert the operator of a possible crossed lead wire situation, but that requires additional time to check connections and to take corrective action. This is a time consuming operation which increases the risk in an emergency situation. Crossed lead wires are a more significant problem when the ECG monitor does not provide interpretation of the recordings and cannot alert the operator of this possibility. In such a case, the ECG signals for each of the twelve leads are recorded on hard copy to be read at a later time. The physician or technician reading the ECG recordings may recognize the error but by that time the patient has usually been disconnected from the monitor. The present invention reduces or eliminates the chances of either of these situations from occurring.

Periodic electrocardiograms are important for providing a cardiographic profile of a patient for early detection and diagnosis of cardiovascular diseases. In order to provide an accurate profile, it is important not only that the electrocardiogram be taken with sensors affixed accurately, but that the sensors be placed at the same location on the patient in the subsequent exam as for the previous examination. The efficacy and the repeatability of the tests is critical so that a series of ECG results can be compared to provide a continuing profile of a patient's medical history for diagnosis and treatment of heart disease.

In urgent situations, including those electrocardiograms taken with the current standard electrode lead wire system, during an acute symptomatic episode there may only be time to attach two to four individual electrodes to the patient. Therefore, it is desirable to have a device which enables more electrodes or sensors to be quickly and accurately secured during such an acute symptomatic episode. Alternatively, it may be necessary to quickly remove some or all of the chest leads when a patient is experiencing a heart attack or in other emergencies in order to administer CPR, to massage the heart, administer drugs, to apply electrical defibrillation paddles, or for other purposes. Accordingly, critical time can be lost both in the removal of the chest leads of the ECG test equipment in order to administer aid to a patient and in their subsequent replacement after aid has been administered.

Because of the inadequacies of prior art devices to solve these problems, there has been a need for a system which: prevents or curtails the possibility of ECG electrode leads or wires from being entangled or crossed; provides quick removal of some of the sensors when it is necessary to administer aid to a patient having a heart attack; provides accurate and appropriate repeatable placement of electrodes at substantially the same location on the patient; accurately and repeatedly obtains signals from electrodes by efficient and effective electrical transmission; and may be attached by persons with varying levels of experience including those with little training.

The inventions disclosed in the above-identified four related applications involve various alternatives for the purpose of trying to effect those goals. The common invention in those applications is a disposable electrode positioning device and utilizes a non-conducting flexible sheet having a predetermined dimensional sensor array. The flexible sheet serves as a template for aligning connectors or sensors, either of the electrode or electrodeless type, on the chest of a patient for transmitting electrical impulses. The sheet has a predetermined dimensional sensor array $V_1$–$V_6$, such that $V_1$ and $V_2$ are positioned approximately on either side of the sternum at the fourth intercostal space, and array $V_3$ is positioned midway between $V_2$ and $V_4$. $V_5$ is equidistant between $V_4$ and $V_6$. The distance between $V_1$ and $V_2$ is predetermined plus or minus a small amount and they are both equidistant from the centerline of the sternum. The distance between $V_2$ and $V_4$ is predetermined plus or minus a small amount, and $V_3$ is located substantially midway between $V_2$ and $V_4$.

An important aspect of the related inventions is that the flexible non-conductive sheet is provided in a plurality of sizes, with each size having arrays $V_1$, $V_2$, $V_3$ and $V_4$, at substantially the same locations and having arrays $V_5$ and $V_6$ at different locations depending on size. In this regard, the locations of $V_5$ and $V_6$ are based on a measured distance between the left midclavicular line and the left midaxillary line on the chest of a patient.

An alternative of the related inventions is that the dimensional array on the flexible non-conductive sheet is provided with cutouts to form a template or mask which is placed on the patient's chest and then conventional electrodes can be positioned in the cutouts. Still another aspect of the related inventions is that the template can be provided with a plurality of conventional tab, snap, or other electrodes affixed on their top sides to the flexible sheet to be placed against the patient's chest. The electrodes are positioned in accordance with the predetermined dimensional array. Small cutouts, or openings, in the template expose the electrode tabs for attaching lead wire clips. Snap electrodes protrude through the template to permit the attachment of lead wire snap connectors.

In a further aspect of the related inventions, the top sides of individual electrodes can be lightly affixed to the flexible sheet of material at the predetermined dimensional array locations. The sheet can be placed on the patient's chest and then peeled away leaving the electrodes properly located on the chest. Each of these concepts can be employed in the new and improved concept of the present invention.

Yet another aspect of those related inventions is a method of sizing a patient for fitting a sensor positioning device having a flexible sheet with a fixed dimensional $V_1$–$V_6$ array positioned in a specific size configuration appropriate for standard electrocardiographic recording. The distance between $V_1$ and $V_2$ is a predetermined distance plus or minus a small amount, and the distance between $V_2$ and $V_4$ is a predetermined distance plus or minus a small amount, with $V_3$ located substantially midway between $V_2$ and $V_4$, and $V_5$ being equidistant between $V_4$ and $V_6$. The method of sizing the disclosed related inventions comprises the steps of measuring the distance between the midclavicular line and a midaxillary line on the chest of the patient, and selecting a positioning device size of those inventions based on the measured distance. This procedure is eliminated by the present invention.

The prior art U.S. Pat. No. 4,583,349 to Manoli and U.S. Pat. No. 5,507,290 to Kelly describe precordial electrodes fixed in a preset pattern on a flexible sheet in positions corresponding to the anatomical landmarks on the patient. The basic problem with all of these inventions is that they require multiple sizes of sensor positioning devices to fit various sized persons.

Manoli envisions, without stating any dimensions, three sizes—a pediatric, medium adult, and large adult—to fit most children and adults within the population. Kelly describes three sizes—small, medium, and large adult-—to fit most adults within the population. Manoli does not describe how one determines which size device a patient would require. Presumably, under Manoli, a small person requires the smallest of the three sizes, i.e., the pediatric, and a large person requires the largest. The invention disclosure is indefinite.

Thus, Manoli does not describe how to size a patient, and it is common for persons placing individual electrodes to make errors. If similar errors are made when sizing the patient for Manoli's device, it is quite likely that the wrong size device would be selected. Once a device is applied to the patient, it would be possible to check the correctness of fit. If wrong, however, i.e., the $V_6$ electrode was located some distance from the patient's midaxillary line, the device would have to be removed and replaced by a more appropriate size device. This trial and error approach wastes time and materials since the first device would need to be discarded without ever being used to take an ECG.

The more recent U.S. Pat. No. 5,678,545 to Stratbucker describes an adhesive sheet having a fixed array of individual electrode groups disposed at varying locations to provide a "one size fits all" system. One embodiment has twelve precordial electrodes with one electrode each at $V_1$, $V_2$, and $V_3$ and groups of three electrodes each at $V_4$, $V_5$, and $V_6$, while other embodiments are suggested for groups of electrodes for other electrode locations in order to achieve a "one size fits all" system.

Stratbucker describes multiple groupings of electrodes for a "single size" system but it is necessary to determine which electrode in each group is within the region of the appropriate location on a patient's chest: for each group of electrodes, there must be a determination of which electrode is closest to the anatomical landmark. Such a determination is time consuming and would at least be impeded by the fact that palpation will be difficult to perform once the sheet is placed over a patient's chest. Moreover, each group of electrodes provides a source for error since there are three electrodes to choose from in each group. Assuming one electrode in each group is most correct, the probability of randomly selecting the best electrode from each of the groups is $0.33^X$, where X equals the number of groups. If there are three groups of electrodes, as described in one embodiment where $V_4$, $V_5$, and $V_6$ consist of groups of three electrodes each, the probability of randomly selecting the appropriate electrode from each group is 0.037, or 1 out of 27 possibilities. Stratbucker relies on a judgment determination for each group of electrodes and therefore selection is time consuming and inexact due to the device physically covering the patient's anatomical features.

Although Stratbucker tries to curtail the possibility of placing conventional individual electrodes far from the region of proper placement by confining the decision to simply selecting one electrode out of each group of three electrodes, medical personnel must still ascertain which electrode is appropriate for each group of electrodes. Not only does this allow for error, it also reduces the chances of consistent electrode placement from one test to the next, thereby confounding any serial comparisons between tests. It also increases the length of time to administer a resting ECG since a separate decision must be made for each group of electrodes.

The present invention uniquely solves these problems by providing a multiple precordial array of sensor electrodes in a single device that will fit essentially all adults and in which sizing is accomplished simply by the determination of the location of a single sensor which is closest to a selected anatomical landmark. This is achieved by the invention of a device having more precordial sensors than the six chest electrodes needed for the resting ECG but significantly less than the number of those taught by Stratbucker. In the present invention, some sensors may serve multiple roles to accommodate different patient sizes within one array by utilizing a particular set of sensors. Each set of sensors corresponds to a specific patient size that can be characterized as small, medium, or large. Once the device of the invention is applied to the patient, one simply and quickly ascertains which of three $V_6$ sensors lies on or closest to the patient's midaxillary line and then connects the electrode/sensor lead wires to the corresponding set of sensors in which the $V_6$ is designated as one of the three selections: small, medium, or large. This greatly simplifies the heretofore universal unresolved problem of instantaneous patient sizing during use, while providing the additional benefits of reducing the cost of production and eliminating the need to stock different size devices.

Another aspect of the present invention is a mask comprised of conductive terminals that are selectively connected to an ECG machine by a single point of attachment or an electronic clip. The clip mechanism includes a means of accurately connecting to any set of terminals by means of a positioning feature on the clip that selectively brings each set of terminals into precise alignment with conducting elements within the clip. Essentially, the selective connection system makes electrical contact with only one set of precordial sensors at a time, i.e., one particular set containing $V_1$ through $V_6$, and excludes the remainder.

Sensors $V_1$ and $V_2$ on the device are centered over the patient's sternum in the left and right fourth intercostal spaces. Once $V_1$ and $V_2$ are applied, all remaining sensors are automatically applied by bringing the flexible sheet down on the patient. The particular $V_6$ sensor closest to the patient's midaxillary line automatically identifies which set of sensors are to be connected to an ECG machine. The clip is then used to selectively connect that set of precordial sensors to the ECG machine.

SUMMARY OF THE INVENTION

The present invention is a disposable universal ECG multiple sensor dermal chest mask for fitting or accommodating different sizes of adult human bodies for performing twelve lead electrocardiograms with repeatability and clinical efficacy of sensor $V_1$, $V_2$, $V_3$, $V_4$, $V_5$, and $V_6$ placement irrespective of the varying human body torso sizes and the different distances between the human body anatomical landmarks. The mask is comprised of a flexible sheet of non-conductive material for carrying nine sensors in a single specific pattern rather than a predetermined fixed array of individual sensor groups or an arbitrary, individually located, array of six precordial sensors needed for a resting twelve-lead ECG. The sheet has nine sensors positioned on it in a specific geometric arrangement with positions $V_1$–$V_4$ being utilized for all sizes of bodies. The $V_5$ position has two independent sensor positions and shares a third with $V_6$. The $V_6$ position has two additional positions whereby when the mask is utilized for a small-size torso, the alternate $V_5$ position closest to the $V_4$ position is utilized along with the shared $V_5$ and $V_6$ position. When the mask is utilized for a medium size torso, the middle alternate $V_5$ position, disposed between the first alternate $V_5$ disposed closest to the $V_4$ position, and between the shared $V_5$ and $V_6$ position, is utilized along with the $V_6$ position disposed between the shared $V_5$ and $V_6$ position and the other remaining $V_6$ position. When the mask is utilized for a large size torso, the shared $V_5$ and $V_6$ position is utilized along with the remaining $V_6$ position.

The present invention also includes a method for sensor placement of six chest sensors typically used for performing twelve-lead electrocardiograms. The steps comprise providing a disposable universal ECG multiple sensor dermal chest mask formed for clinically efficacious placement of six precordial leads on a patient's chest irrespective of torso size. The mask has a multiplicity of sensors which are arranged in a specific geometric pattern whereby as few as nine sensors can be utilized to serve as sensors for at least three different classes of sizes of human torsos. The mask includes indicia for aligning it on both the centerline of the patient's sternum and the fourth intercostal space whereby at least three sets of sensors on the mask, comprising six sensors, each accommodate three different classes of sizes of human torsos. Six of the nine sensors for performing an ECG are selected depending upon the torso size of the patient, and sensor leads from the ECG test apparatus are connected to the six selected sensors.

OBJECTS OF THE INVENTION

It is therefore an important object of the present invention to provide an ECG multiple sensor positioning device which is universal whereby one size fits all rather than requiring a multitude of different sizes thereby achieving economic benefits of high volume production and simplified sales and distribution.

It is another object of the present invention to provide a universal ECG sensor mask and method of use in which less time is needed to perform an ECG since the steps used to determine which mask size to utilize are eliminated.

It is a further object of the present invention to provide a disposable universal ECG sensor positioning device which can be thrown away after use providing less risk of transmitting infection and one in which the logistics of maintaining different size devices in inventory are eliminated.

It is still another object of the present invention to provide a universal ECG sensor mask and method of use in which, simplified, efficacious, and repeatable sensor placement results are guaranteed.

It is yet a further object of the present invention to provide a multiple sensor mask and method of use in which a twelve-lead electrocardiogram, which provides the most comprehensive recordings of electrical activity of the heart for recognizing ischemic electrocardiographic changes, can be obtained quickly and repeatably from a single size mask.

And it is still another object of the present invention to provide a universal ECG electrode mask and method of use in which three different ECGs can be performed by the same device.

Other objects and advantages of the present invention will become apparent when the method and apparatus of the present invention are considered in conjunction with the accompanying drawings.

DESCRIPTION OF THE PREFERRED EMBODIMENT

Figure 1:
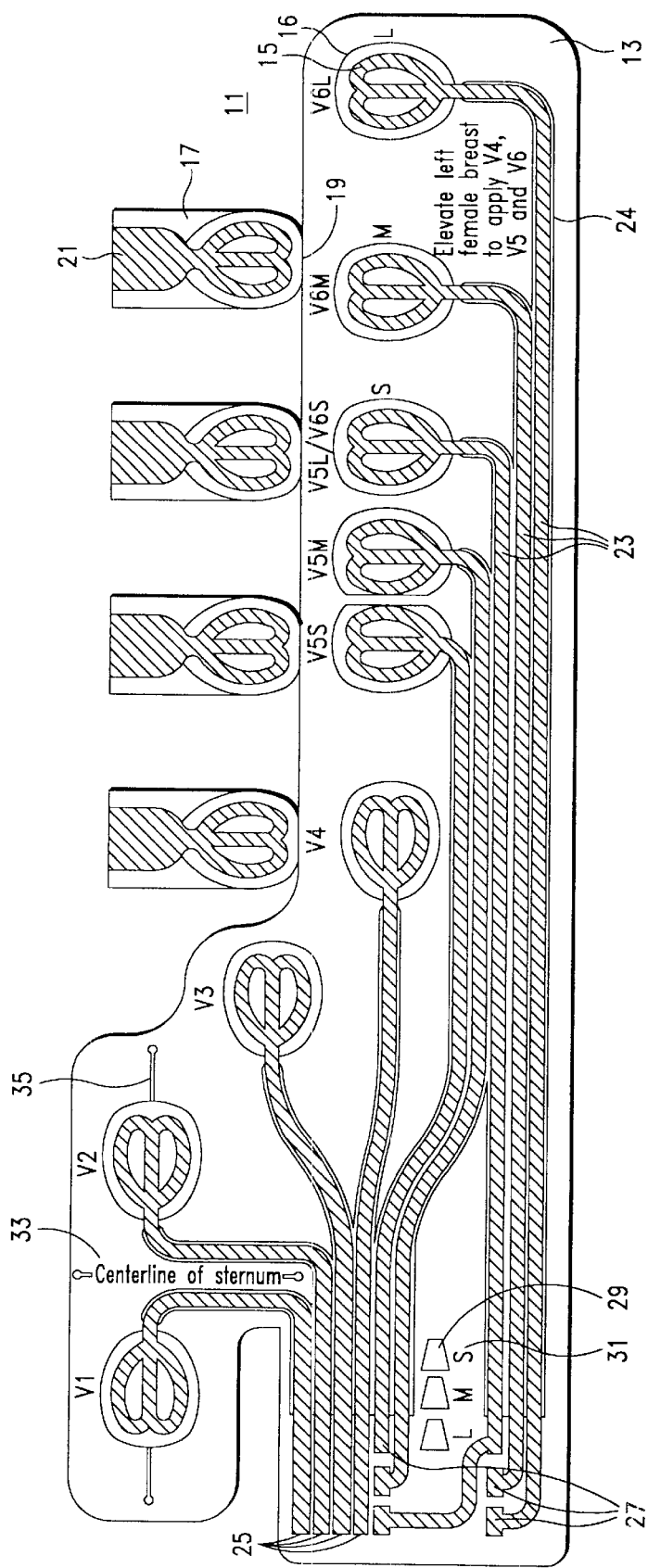
FIG. 1 is a plan view of the Universal ECG Sensor Positioning Device of the present invention.

Reference is made to the drawings for a description of the preferred embodiment of the present invention wherein like reference numbers represent like elements on corresponding views.

FIG. 1 illustrates a plan view of the universal disposable ECG sensor positioning device of the present invention for placement on the chest of a patient for performing an ECG test. The word "universal" as used in describing the device is an abbreviation of the descriptive colloquial terminology—one size fits all. In actuality, the device of the present invention fits ninety percent (90%) or more of the adult population and most older children as well. The term "disposable" means that the device is intended for a single or one time use only. However, the physical form of the device could be reusable for more than one test, and a more permanent embodiment of the design could be a truly reusable device possibly requiring sterilization, cleaning, and/or fresh adhesive for reuse. Therefore, the term "disposable," as used in the descriptive preamble of the claims, is provided solely as an aid for most accurately describing the preferred embodiment of the invention in relation to the prior art and should not be interpreted as a limitation on the forms of the invention and scope of the claims.

The device is a dermal chest mask 11 which is formed of a sheet of flexible non-conducting material 13 for carrying or positioning nine chest electrodes or electrodeless sensors 15, or simply holes therein for the positioning thereof, for connection by electrical lead wires (not shown) to a standard electrocardiographic diagnostic machine. The flexible non-conductive web or sheet may be formed from any preferably transparent natural or synthetic material which is capable of accepting a print. Generally any cellulosic material, polyester, polyolefin, polyvinyl chloride, nylon or mixtures thereof would be suitable. Cotton, polypropylene, or polyethylene can be used if cost is a consideration. However, polyester is likely the most preferable.

While the most practical form of the invention incorporates the ECG sensors 15 into the flexible sheet 13, a less sophisticated form of the invention can utilize simply the specific arrangement of sensor positioning taught herein by the placement of holes for the electrodes in the specific geometric pattern called for herein on the sheet. The standard ECG electrodes can then be placed in the holes and adhered to the patient's skin through the holes. Other masks using the specific sensor positioning arrangement and indicia of the present invention are also contemplated as within the scope of the invention.

Detachable limb lead sensors 17 can also easily be provided integral to the mask during the manufacturing process. In a preferred embodiment, they are formed integral to the mask with a means for easy detachment such as a set of perforations along the line of joinder 19 of the limb lead sensor to the mask 11. The ends of the limb lead sensors are provided with an electrical contact area 21 whereby an electrical lead can be connected to the sensor by any appropriate means such as an electrical connector clip.

The receptor sensor electrodes 15, which are positioned on the mask 11, are spaced relative to each other in a specific geometric configuration appropriate for electrocardial recordings from all sizes of adult human torsos. Each receptor sensor or electrode is adapted for electrical connection with the skin of a patient's body for detecting and transmitting electrical signals generated by the patient. The mask includes conductor strips 23 each of which extends to and electrically connects to a sensor. The other end of each conductor strip terminates in a connector end or terminal which engages any type of connection or cable junction for electrical connection with the electrocardiograph analyzer.

Three discrete electrical contact or terminal area groups are provided for connection to an ECG machine to accommodate three different classes of adult human torso sizes. The four individual terminals 25 for $V_1$ to $V_4$ are contiguous, and six discrete terminals 27 are provided for $V_5$ and $V_6$ in three sizing configurations.

The terminal ends of the strips are preferably disposed adjacent to each other in three identical patterns to facilitate connection to a common connector which can be utilized for all three classes of sizes. A customized clip is envisioned to simplify use of the mask of the present invention by permitting a single-clip connection. Pin locator cut-outs 29 and indicia 31 for the clip allow it to be selectively engaged to the mask for connecting a certain or selected set of six sensors to the ECG machine.

In order to establish electrical connection between a human body and the receptor sensors 15, a biocompatible electrically conductive adhesive, such as hydrogel, is applied to the body contacting side of the sheet at each sensor site for adhesion to the skin of the patient. It is generally transparent and shown in outline 16 in the drawings. Hydrogel is commercially available as are other suitable conductive adhesives and any suitable electro-dermal adhesive would serve the purpose. The size of the adhesive area is generally between 3 and 9 square centimeters. When the mask is pressed against the skin of the patient's chest, the sensors are electrically connected to the patient at each receptor.

The gel-coated adhesive area of the mask 11 includes at least one release liner in releasable adhesive contact with the gel covering the sensors 15. Because the release liner can be transparent, and is simply a sheet of material, it is not shown in the drawings. Separate release liners could be provided for each sensor, but in the preferred embodiment, a single release liner covers all of the sensors and the mask can be removed from the liner in a single operation to expose all of the sensors as a unit (except for the limb lead sensors). The limb lead sensors 17 are released individually having been separated at the perforations 19 along the line of joinder with the mask. The flexible release liner covering the receptors may be made from a suitable dielectric film or coated paper which includes polypropylenes, polyesters, olefinic polymers, polyvinyl chloride and its copolymers, acrylic rubbers, ABS resin, and the like. Commercial suppliers for these materials are listed in the related applications.

The receptor electrodes 15 and the conductor strips 23 can be produced from any electrically conductive material, e.g., metal, foils, conductive polymers, graphite, carbon fibers, and the like. They include gold, copper, silver, tin, aluminum, N-vinyl pyrrolidone, and alloys or mixtures thereof. The receptor/conductors can also be made from a conductive paste of a metal in particle form in a suitable binder which is printed or silk screened onto the flexible non-conductive sheet or electrolessly deposited. A connective polymer may be heat pressed or otherwise conventionally secured to the web or sheet.

Copper strips could be utilized and electrolessly deposited on the polymeric sheets in a range of thickness from about 0.25 to about 5 microns, more preferably from 0.25 to 1.5 microns, and most preferably 0.4 microns in thickness. A metallic ink may be preferable such as a commercially available silver ink. Each of the conductor strips are less than 10, and preferably less than 5, micrometers in thickness, whereby the flexibility of the connector and adhesion of the gel surface to the skin are substantially enhanced.

The exposed conductive strips 23 may be partially covered with a dielectric layer for insulating the conductive pathways. This coating can be transparent and is also shown in the drawings in outline 24. The strips are coated with a dielectric polymeric material in such a way so that only selective portions comprising the sensor 15 and the electrical contact or terminal areas 25, 27 are exposed. Suitable dielectric coatings include polyesters, ethylene-vinyl acetate copolymers, polyvinyl chloride and its copolymers, terpolymers such as acrylonitrile-butadiene styrene (ABS resins) and inter alia.

Therefore, a preferred laminate for the flexible sheet of the invention can comprise several layers, several of which can be transparent. A preferred embodiment of the invention would include: (1) a base layer of a flexible non-conductive film of polyethylene terphthalate; (2) a bond layer for the conductor strips such as a catalyst in contact with a conductive ink; (3) a conductor strip comprised of silver ink; (4) an adhesive layer such as hydrogel superimposed upon the silver ink in the sensor areas of the mask, or alternatively, a dielectric layer superimposed upon the silver ink in the conductor strip area of the mask; and (5) a flexible release liner as the top layer superimposed upon at least the adhesive layer of the mask.

Since the device of the present invention is designed for use by untrained personnel as well as a trained individual, the sheet material of the mask contains designator markings or indicia to simplify attaching to or positioning of the mask on the patient's chest. It is sufficiently self-describing such that it allows a person untrained in electrocardiography to position the mask to obtain highly reliable and repeatable ECG signals. It also includes indicia for sizing the patient.

FIG. 1 shows the sensor array ($V_1$, $V_2$, $V_3$, $V_4$, two $V_5$s, a $V_5$ and $V_6$ shared, and two $V_6$s) and the indicia therefor. Indicia $V_1$, $V_2$, $V_3$, and $V_4$ indicate a single position for each sensor. Indicia V5S indicates $V_5$ small; V5M indicates $V_5$ medium, V5L/V6S indicates either $V_5$ large or $V_6$ small. V6M and V6L correlate to $V_6$ medium and large, respectively. The S, M, and L indicia are provided to aid in selecting which set of sensors are to be utilized. The additional indicia between V6M and V6L aid the user in positioning the mask. The indicia 31 proximate the pin locator cut-outs 29 aid in selecting the electrical connection for sensor set selection.

Nine sensors 15 are arranged in a precordial sensor array of three sets of six sensors each in which certain of the sensors serve the same function in each of the sets of six and at least one of the sensors serves as a different designated sensor in the different sets. The nine precordial sensors are disposed in a specific universal geometric arrangement rather than in predetermined fixed arrays of individual classes of sizes of sensor groups, as taught in the related cases and the Kelly and Manoli patents, or in multiple all-inclusive sensor group arrays as taught by the Stratbucker singular patent. Nor are they positionable in an arbitrary individually located array of six precordial sensors as would be placed by a technician for a resting ECG. In the present invention, nine sensors form three sets of sensor groups including three positions for each of the $V_5$ and $V_6$ in which one sensor serves for either $V_5$ or $V_6$ in two different sensor sets whereby three sets of six sensors each are provided by the nine sensors to position six of the sensors proximate to the anatomical landmarks of three different classes of human torso sizes.

The sensors 15 are disposed on the flexible sheet 13 which is designed to adhere to a human torso so that the receptor sensors are located upon the precordial area of the chest and above the epigastric region of the abdomen. The flexible sheet can be essentially transparent and also includes self-explanatory indicia 33 for aligning the mask on both the centerline of the patient's sternum and on the fourth intercostal space 35 whereby at least three sets of sensors on the mask, comprising six sensors each, accommodate three different classes of human torso sizes. In addition to facilitating correct placement of the receptors on the precordial areas of the human torso, the indicia also provide for selecting the correct set of sensors for the torso size and show which sensors are to be used. Indicia 29, 31 for the electrical connections to the ECG machine are also essentially self-explanatory and are accordingly based on the selected torso size of the patient. The precordial indicia indicate which sets of sensors correlate to which torso size and that one of the sensors is shared or utilized for two classes of torso sizes but numbered as different designation sensors, $V_5$ or $V_6$.

When the electro-dermal connectors are properly positioned for attachment to a patient, the position of the receptors at $V_1$ and $V_2$ are disposed to lie approximately on opposite sides of the patient's sternum at the fourth intercostal space as shown by the indicia 33, 35. The receptors at $V_3$ and $V_4$ are attached over the ribs, with $V_3$ positioned approximately equidistant between $V_2$ and $V_4$ and $V_4$ positioned approximately over the intersect of the fifth intercostal space and the left midclavicular line. The receptors at $V_5$ and $V_6$ are placed at the side of the torso so that $V_5$ is substantially midway between $V_4$ and $V_6$.

In positioning the array of receptors for the preferred embodiment of the present invention, it has been found that the distance between $V_1$, $V_2$, $V_3$, and $V_4$ can be consistent for all sizes of human torsos. The dimensions between $V_1$, $V_2$, $V_3$, and $V_4$ have been developed to accommodate nearly all adults within tolerances acceptable for the resting ECG. It has also been found that body placement for connectors $V_5$ and $V_6$ vary depending on individual size. These variations are uniquely accommodated in one size mask by the present invention.

There is a novel method provided by the present invention for determining the proper size selection of electrode sets, i.e., for selecting six of the nine sensors for performing an ECG depending upon the torso size of the patient. The selection of the six sensors is ascertained by determining which one of the same designation sensors in each set lies closest to a selected precordial landmark whereby the set containing that closest lying sensor is selected as the set of six sensors to be utilized. As with $V_1$–$V_4$, it has been determined that the distance from the $V_4$ position to the $V_6$ position determines the size of a patient. For the inventions disclosed in the four related applications, the measurement of this distance is determined by having the applying technician measure, such as by using his/her thumb and the middle finger, the distance between the midclavicular line and the midaxillary line on the chest of the patient. This distance is then compared to a sizing scale to select the proper size of device. The present invention, however, does not require any type of intermediate step to determine a patient's size. Rather, the device is applied to the patient and a simple visual observation ascertains which of three $V_6$ sensors lies closest to the patient's midaxillary line to establish that patient's size.

The distance between $V_4$ to $V_6$, that is, the distance between the midclavicular line and the midaxillary line on the patient, varies within predetermined limits based on the size of the torso. For a small size, the distance between $V_4$ and $V_6$ can range from about 2.5 to 4.5 inches; for the medium size, the distance can range from about 4.0 to 6.0 inches; and, for the large size, the distance can range from about 6.0 to 8.0 inches.

In the present invention, sensors $V_1$, $V_2$, $V_3$, and $V_4$ re positioned the same for all sizes of torsos. The center of $V_1$ is located on a point generally about 2.0 inches from the center of $V_2$ approximately on the 270 degree radial from the center of $V_2$ wherein the radial is measured with zero degrees measured from north at the top of $V_2$. The center of $V_4$ is located on a point generally 3.5 inches from the center of $V_2$ approximately on the 125 degree radial from the center of $V_2$. The center of $V_3$ is in line with $V_2$ and $V_4$ and is located on a point substantially between the center of $V_2$ and the center of $V_4$. The receptors $V_5$ and $V_6$ have three alternative positions each: all of the positions being disposed in the 90 degree radial from $V_4$. The centers of the $V_5$ positions are located approximately 1.75, 2.5, and 3.5 inches from $V_4$ and the centers of the $V_6$ positions are located approximately 3.5, 5.0, and 7.0 inches from $V_4$ whereby the centers of both $V_5$ and $V_6$ which are both located approximately 3.5 inches from $V_4$ share a common sensor in different sets of sensors.

The table below corresponds to the determined measurements for electrode placement which are all inherent in the present invention. It shows the preferred dimensional layout for $V_5$ and $V_6$ relative to $V_4$ for different sized torsos. Obviously, small variations in the lengths of the measurements are within the scope of the invention:

TABLE I

| Size | $V_4 - V_5$ | $V_5 - V_6$ | $V_4 - V_6$ |
| --- | --- | --- | --- |
| Small | 1.75" | 1.75" | 3.5" |
| Medium | 2.5" | 2.5" | 5.0" |
| Large | 3.5" | 3.5" | 7.0: |

The distance between $V_1$ and $V_2$ is 2.0 inches, the distance between sternum centerline and $V_4$, along a horizontal line is 3.85 inches, and the distance between $V_2$ and $V_4$ along a vertical line is 2.0 inches, although this vertical distance could be up to 3.5 inches without considerably altering the effectiveness of the device. In addition, $V_3$ is located on a diagonal line between $V_2$ and $V_4$, and is equidistant from $V_2$ and $V_4$. These variations can be combined to create a universal mask by the use of only nine sensors to accommodate practically any size adult person. A reduction in the number of sensors required is an important consideration in manufacturing cost efficiency.

The mask of the present invention provides a plurality of connectors or terminals arranged in a predetermined dimensional array $V_1$–$V_6$ on the flexible sheet which inherently observes the dimensions dictated by Table I. In providing alternative locations of the sensors, the dimensional array on the flexible sheet becomes universal and the specific size configuration of the dimensional array or layout on the flexible sheet is determined in the same manner as for multiple sizes of masks to permit the production of an accurate electrocardial recording during ECG testing which can be reliably repeated.

The nine sensors are positioned on the sheet in a geometric pattern approximating the standard precordial anatomical landmarks of any adult human being. The positioning of sensors $V_1$–$V_4$ is the same for all sizes of torsos. The position of $V_5$ has two independent sensors and it shares a third with $V_6$. The position of the $V_6$ sensor has two additional positions spaced apart from the shared sensor with $V_5$. All of the $V_5$ and $V_6$ sensors lie along the same line with, and spaced from, the $V_4$ sensor.

When the mask is utilized for a small size torso, the alternate $V_5$ sensor position closest to the $V_4$ position is utilized along with the shared $V_5$ and $V_6$ sensor position. When the mask is utilized for a medium size torso, the middle alternate $V_5$ sensor position, disposed between the first alternate $V_5$ sensor disposed closest to the $V_4$ position, and between the shared $V_5$ and $V_6$ sensor position, is utilized along with the $V_6$ sensor position disposed between the shared $V_5$ and $V_6$ sensor position and the other remaining $V_6$ sensor position. When the mask is utilized for a large size torso, the shared $V_5$ and $V_6$ sensor position is utilized along with the remaining $V_6$ sensor position which is located furthest from $V_4$. The shared $V_5$ and $V_6$ sensor functions as $V_6$ when the mask is utilized for a small-size torso, and functions as $V_5$ when utilized for a large-size torso. The sensor set selected for performing the ECG on a specific patient is recorded for the taking of subsequent ECGs on that patient to insure repeatability of sensor placement.

The present invention also contemplates a method of sensor placement for performing twelve-lead electrocardiograms by means of a disposable universal multiple sensor ECG dermal chest mask for fitting or accommodating different sizes of adult human bodies with repeatability and clinical efficacy of sensor $V_1$, $V_2$, $V_3$, $V_4$, $V_5$, and $V_6$ placement irrespective of the varying human body torso sizes and the different distances between the human body anatomical landmarks. The method of sensor placement is comprised of several steps. A mask is provided which is formed for clinically efficacious placement of six precordial sensors on a patient's chest irrespective of torso size. It has a multiplicity of precordial sensors disposed in a specific geometrical pattern rather than in predetermined fixed arrays of individual sensor groups or an arbitrary individually located array of six precordial sensors. As few as nine sensors can be utilized to serve as sensors for at least three different classes of human torso sizes.

In the preferred method of the invention, the mask is provided with an arrangement of nine sensors which are arranged in three sets of six sensors each in which certain of the sensors serve the same function in each of the sets and at least one of the sensors serves as a different designated sensor in the different sets. In the preferred embodiment of the invention, the nine sensors form three sets of sensor groups which include three positions for each of the $V_5$ and $V_6$ positions. In one group, one sensor services for either $V_5$ or $V_6$ in two different sensor sets whereby three sets of six sensors each are provided by the nine sensors to position six of the sensors proximate the standard precordial anatomical landmarks of three different classes of sizes of human torsos. The mask is provided with indicia for positioning it on a patient's sternum centerline and the fourth intercostal space and for determining which sensors correspond to the three sensor sets.

The mask is placed on a patient's chest and the positioning indicia on the mask are aligned with the corresponding anatomical positions on the patient's chest. Six of the nine sensors are then selected for performing an ECG depending upon the torso size of the patient by determining which one of the same designation sensors in each set lies closest to a selected precordial landmark whereby the set of sensors containing the closest lying sensor is selected as the set of six sensors to be utilized. In the preferred embodiment of the invention, this is done by ascertaining which of the three $V_6$ positions lies on or closest to the patient's midaxillary line. Sensor leads from ECG test apparatus are connected to the corresponding set of sensors which include the identified $V_6$ position.

Thus, in summary, both an apparatus and methods for torso sizing and sensor placement for performing twelve-lead electrocardiograms are provided, and the stated objects of the present invention are achieved. A single mask design, having only nine sensors instead of three different sizes of masks as taught by the prior art, provides a universal size which can be utilized to obtain the benefits of simplified high volume production in order to lower the cost to the user and reduce the time previously needed to establish the size of a patient. The preferred embodiment of the present invention solves the problems associated with high variability of individual sensor placement which may produce inaccurate ECGs, and thus an incorrect diagnosis, and which problems prevent valid and reliable serial comparisons between repeat ECGs on the same patient.

The present invention eliminates the logistics of maintaining different size sensor masks. This includes the stock in the central supply of a hospital, stock rooms of wards and clinics, and individual ECG carts. A related benefit is that stock would be depleted evenly thereby eliminating the possibility that some stock, e.g., a less often used size in a three-size system, might not be used prior to reaching an expiration date. The one size design of the present invention eliminates the steps required to determine a patient's torso size. Any possibility of error when sizing a patient is eliminated.

The method of the present invention is one in which there is less waste since nearly all adult patients are accommodated by the one device. With more than one device size, there is the possibility that a wrong size would be applied to a patient and would need to be removed and discarded prior to applying the correct size device. This trial and error situation would also increase the time spent performing an ECG on one patient. This is eliminated by the present invention.

The mask and method of use of the present invention in which the additional sensors with their respective adhesive areas increase the total area adhered to the patient. This will reduce the tension on each individual sensor since any pulling caused by respiration or from the ECG cable assembly will be shared by a greater number of sensors than would exist with a six-sensor precordial pad. It is generally understood that too much tension on a sensor decreases its performance.

It is also an object of the present invention to permit the taking of three different ECGs simultaneously with the same device. Because the device contains three precordial sensor patterns, it is possible to take three different ECGs by connecting to each pattern in turn by simply reapplying the single six-conductor connectors serially to the three terminal sets. This may provide additional diagnostic information beyond what is now obtained from a conventional ECG using six precordial sensors.

Thus it will be apparent from the foregoing description of the invention in its preferred form that it will fulfill all the objects and advantages attributable thereto. While it is illustrated and described in considerable detail herein, the invention is not to be limited to such details as have been set forth except as may be necessitated by the appended claims.

We claim:

1. A method for obtaining an electrocardiogram by means of a universal ECG multiple sensor dermal precordial mask incorporating sensors $V_1$, $V_2$, $V_3$, $V_4$, $V_5$, and $V_6$ for fitting different sizes of human bodies, said method comprising the steps of providing a mask having at least nine precordial sensor positions forming at least three sets of sensor groups including three positions for each of said $V_5$ and $V_6$ sensors, wherein said nine sensor positions are disposed in a specific geometric arrangement with said $V_1$–$V_4$ being utilized for all sizes of bodies, said $V_5$ position having two independent sensor positions and sharing a third with said $V_6$ position, and said $V_6$ position having two additional positions, said mask including indicia for determining which sensor positions correspond to said three sensor sets, aligning said mask on a patient's chest so that said $V_1$ and $V_2$ are disposed approximately on opposite sides of the patient's sternum, ascertaining from said indicia which of said three $V_6$ sensor positions lies on or is closest to the patient's midaxillary line, and obtaining electrocardiographic information from the corresponding set of sensors which include said $V_6$ sensor.

2. A mask as set forth in claim 1, wherein when said mask is utilized for a small size torso, the alternate $V_5$ sensor position disposed closest to said $V_4$ position is utilized along with said shared $V_5$ and $V_6$ position, when said mask is utilized for a medium size torso, the middle alternate $V_5$ sensor position, disposed between said first alternate $V_5$ position disposed closest to said $V_4$ position, and between said shared $V_5$ and $V_6$ position, is utilized along with said $V_6$ position disposed between said shared $V_5$ and $V_6$ position, and the other remaining $V_6$ position, and when said mask is utilized for a large size torso, said shared $V_5$ and $V_6$ sensor position is utilized along with said remaining $V_6$ position.

3. A universal ECG multiple sensor dermal precordial mask for fitting different sizes of human bodies for obtaining electrocardiographic information using sensors $V_1$, $V_2$, $V_3$, $V_4$, $V_5$, and $V_6$, said mask comprising a sheet of non-conductive material incorporating at least nine sensor positions forming three sets of sensor groups including three positions for each $V_5$ and $V_6$ positions, said nine sensor positions being disposed in a specific geometric arrangement with said $V_1$–$V_4$ positions being utilized for all sizes of bodies, said $V_5$ position having two independent sensor positions and sharing a third with said $V_6$ position and said $V_6$ position having two additional positions.

4. A mask as set forth in claim 3, wherein said sheet is disposable.

5. A mask as set forth in claim 3, wherein said sheet is flexible.

6. The mask as set forth in claim 3 wherein said $V_1$ and $V_2$ sensor positions are disposed equidistant from the patient's sternum and on the fourth intercostal space, the center of said $V_1$ position is located approximately 2.0 inches from the center of said $V_2$ position on the 270 degree radial therefrom, the center of said $V_4$ position is located approximately 3.5 inches from the center of said $V_2$ position on the 125 degree radial therefrom, the center of said $V_3$ position is disposed on a line and equidistant between said $V_2$ and said $V_4$ positions, and said $V_5$ and $V_6$ positions have three alternative positions each, all of said positions being disposed on a 90 degree radial from said $V_4$ position, the centers of said $V_5$ positions being located 1.75, 2.5, and 3.5 inches therefrom and the centers of said $V_6$ positions being located 3.5, 5.0, and 7.0 inches therefrom whereby the centers of said $V_5$ and $V_6$ positions which are both located 3.5 inches from said $V_4$ position share a common position in the different sets of sensors.

* * * * *